United States Patent [19]

Stadler et al.

[11] 4,393,051

[45] Jul. 12, 1983

[54] 1-N(AMINOPOLYHYDROXYALKYL-)AMINOGLYCOSIDE ANTIBIOTICS AND METHOD OF USE

[75] Inventors: Peter Stadler, Haan; Karl G. Metzger, Wuppertal; Eckart Voss, Cologne; Uwe Petersen, Leverkusen; Hans-Joachim Zeiler, Velbert, all of Fed. Rep. of Germany

[73] Assignee: Bayer Aktiengesellschaft, Leverkusen, Fed. Rep. of Germany

[21] Appl. No.: 155,896

[22] Filed: Jun. 2, 1980

[30] Foreign Application Priority Data

Jun. 19, 1979 [DE] Fed. Rep. of Germany ....... 2924659

[51] Int. Cl.$^3$ ..................... A61K 31/71; C07H 15/22
[52] U.S. Cl. ................................ 424/180; 536/13.6; 536/13.9; 536/16.8
[58] Field of Search ............ 424/180; 536/17 R, 13.6, 536/13.9, 16.8

[56] References Cited

U.S. PATENT DOCUMENTS

| | | | |
|---|---|---|---|
| 4,029,882 | 6/1977 | Wright | 536/17 R |
| 4,044,123 | 8/1977 | Daniels et al. | 536/17 R |
| 4,053,591 | 10/1977 | Daniels et al. | 536/10 |
| 4,107,435 | 8/1978 | Ross | 536/17 R |
| 4,160,082 | 7/1979 | Million et al. | 536/17 R |
| 4,190,722 | 2/1980 | Voss et al. | 536/17 R |
| 4,199,572 | 4/1980 | Schroder et al. | 424/180 |
| 4,224,315 | 9/1980 | Stadler et al. | 536/17 R |
| 4,235,888 | 11/1980 | Stadler et al. | 424/180 |

FOREIGN PATENT DOCUMENTS

| | | | |
|---|---|---|---|
| 2708008 | 9/1977 | Fed. Rep. of Germany | 536/17 R |
| 2292482 | 11/1975 | France | 536/17 R |
| 2305190 | 5/1976 | France | 536/17 R |
| 2348223 | 4/1977 | France | 536/17 R |
| 2383963 | 3/1978 | France | 536/17 R |

OTHER PUBLICATIONS

Suzuki et al., "Chem. Abst.", vol. 87, 1977, p. 53534(e).
Muller, "Houben Weyl", 4th Ed., vol. XI.

*Primary Examiner*—Johnnie R. Brown
*Attorney, Agent, or Firm*—Sprung, Horn, Kramer & Woods

[57] ABSTRACT

The invention relates to pseudotrisaccharides of Formula (I) as defined above, methods for preparing them, compositions containing them and methods for the use of said compounds and compositions.

12 Claims, No Drawings

1-N(AMINOPOLYHYDROXYALKYL)AMINO-GLYCOSIDE ANTIBIOTICS AND METHOD OF USE

The invention relates to new pseudotrisaccharide compounds, processes for their production and to their use as medicaments.

The invention particularly relates to new, antibacterially active aminoglycoside antibiotics of the 4,6-di-O-(aminoglycosyl)-1,3-diaminocyclitol type.

Aminoglycoside antibiotics are important substances for effectively combating bacterial infection. However, in many cases the appearance of resistant germs reduces their broad applicability; furthermore, side effects, such as, for example, ototoxicity and nephrotoxicity, can also occur. In some cases it is possible to eliminate these disadvantages by forming derivatives.

According to the present invention there are provided compounds which are pseudotrisaccharides of the formula (I)

or a salt thereof, in which
X denotes a radical of the general

Y denotes a radical of the formula

U and V both denote hydrogen atoms, or one denotes a hydrogen atom and one denotes a hydroxyl group and
W and Z both denote hydrogen atoms, or one denotes a hydrogen atom and one denotes a hydroxyl group, or
Z denotes $NHR_6$ and
W denotes a hydrogen atom, and in which
$R_1$, $R_2$, $R_3$, $R_4$, $R_5$ and $R_6$ independently of one another denote a hydrogen atom or a radical of the formula $$CH_2-(CH_2)_{n1}-\underset{BR_7}{(CH)_{n2}}-A_{n3}-\underset{BR_7}{(CH)_{n4}}-CH_2R_8$$

in which
A denotes a radical of the formula $$\left[\underset{(CH_2BR_7)_{n5}}{CH_{(2-n5)}}\right]$$

each $R_7$ independently denotes a hydrogen atom or an alkyl or acyl group, or
2 radicals $R_7$ together denote an alkylidene radical,
$R_8$ denotes a hydrogen atom or $BR_7$,
B denotes O or NH, with the condition that at least one B denotes O and one B denotes NH and the number of the groups NH for B does not exceed 2,
$n_1$ is 0, 1, 2 or 3,
$n_2$ is 0, 1, 2, 3, 4 or 5 and
$n_3$, $n_4$ and $n_5$ independently of one another are 0, 1 or 2,
the sum of $n_1$, $n_2$, $n_3$ and $n_4$ being values 1 to 5, the total number of $BR_7$ groups in at least one of the radicals $R_1$, $R_2$, $R_3$, $R_4$ and $R_5$ being 2 to 6 and at least one of the radicals $R_1$, $R_2$, $R_3$, $R_4$ and $R_5$ being other than a hydrogen atom.

Compounds according to the invention which are of particular interest are those which are derived from the antibiotics gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, JI-20A, JI-20B, verdamicin G52, G418, 66-40D, mutamicin 1, mutamicin 2, mutamicin 4, mutamicin 5 and mutamicin 6.

Of these, the sisomicin derivatives represented by formula (II)

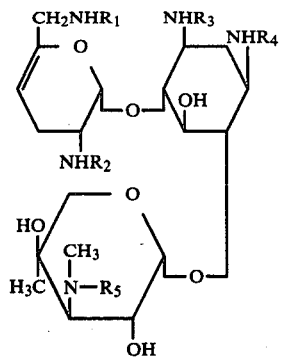

or a salt thereof, in which $R_1$, $R_2$, $R_3$, $R_4$ and $R_5$ have the meaning indicated above, are particularly valuable.

$R_7$ when alkyl is preferably $C_1$ to $C_4$ alkyl, and when acyl is preferably $C_1$ to $C_4$ alkylcarbonyl, formyl or benzoyl.

Alkylidene formed by 2 radicals $R_7$ is preferably $C_1$ to $C_6$ alkylidene.

Preferred compounds within the formula (I) are those in which $R_4$ and one of the radicals $R_1$ and $R_2$ are other than hydrogen and the radicals $R_3$, $R_5$, $R_6$ and the other one of the radicals $R_1$ and $R_2$ denote hydrogen. Very particularly preferred compounds are those in which $R_1$, $R_2$, $R_3$, $R_5$ and $R_6$ denote hydrogen and $R_4$ is other than hydrogen.

Amongst these compounds, those compounds in which $n_3$ and $n_4$ are 0 and the sum of $n_1$ and $n_2$ is 1, 2 or 3 are of particular interest.

The compounds according to the invention exhibit powerful anti-bacterial properties against a large number of germs and are exceptionally well tolerated.

Among the new pseudotrisaccharide salts of the invention, those salts that are pharmaceutically acceptable are particularly important and are preferred.

The new free pseudotrisaccharides of the general formula (I) and their salts can be interconverted in any suitable manner; methods for such interconversion are known in the art.

The pharmaceutically acceptable salts are preferably derived from inorganic or organic acids, such as sulphuric acid, phosphoric acid, nitric acid, hydrochloric acid, hydrobromic acid, acetic acid, propionic acid, ascorbic acid, citric acid and the like to form acid-addition salts.

Examples of suitable radicals $R_1$ to $R_6$ are straight-chain aminopolyhydroxyalkyl radicals, such as 2-amino-3,4,5,6-tetrahydroxyhexyl, 3-amino-2,4,5,6-tetrahydroxyhexyl, 4-amino-2,3,5,6-tetrahydroxyhexyl, 5-amino-2,3,4,6-tetrahydroxyhexyl, 6-amino-2,3,4,5-tetrahydroxyhexyl, 2-amino-3,4,5-trihydroxypentyl, 3-amino-2,4,5-trihydroxypentyl, 4-amino-2,3,5-trihydroxypentyl, 5-amino-2,3,4-trihydroxypentyl, 3-amino-2,4-dihydroxybutyl, 4-amino-2,3-dihydroxybutyl, 2-amino-3,4,5-trihydroxyhexyl, 3-amino-2,4,5-trihydroxyhexyl, 4-amino-2,3,5-trihydroxyhexyl, 5-amino-2,3,4-trihydroxyhexyl, 3-amino-4,5-dihydroxypentyl or 3-amino-4,5-dihydroxyhexyl, diaminopolyhydroxyalkyl radicals, such as 2,3-diamino-4,5,6-trihydroxyhexyl, 3,6-diamino-2,4,5-trihydroxyhexyl or 2,3-diamino-4,5-dihydroxypentyl, and N-alkylated or N-acylated aminopolyhydroxyalkyl radicals, such as 2-methylamino-3,4,5,6-tetrahydroxyhexyl, 3-methylamino-2,4,5,6-tetrahydroxyhexyl, 5-methylamino-2,3,4,6-tetrahydroxyhexyl, 2-methylamino-3,4,5-trihydroxypentyl, 4-methylamino-2,3,5-trihydroxypentyl, 5-methylamino-2,3,4-trihydroxypentyl, 6-hydroxyethylamino-2,3,4,5-tetrahydroxyhexyl, 3-dimethylamino-2,5-dihydroxyhexyl, 2-acetylamino-3,4,5,6-tetrahydroxyhexyl, 2-ethoxycarbonylamino-3,4,5,6-tetrahydroxyhexyl, 3-acetylamino-2,4,5-trihydroxypentyl or 5-ethylamino-1,3,4-trihydroxypentyl, and also O-alkylated aminopolyhydroxylated radicals, such as, 5-amino-2,3,4-trihydroxy-6-methoxyhexyl.

The radicals listed above are to be understood only as examples. They all contain at least one, and in most cases several, chiral C atoms and exist in the form of optically pure diastereomers or as diastereomer mixtures. It can be advantageous to use the compounds according to the invention as optically pure products.

Examples of the active compounds according to the invention which may be mentioned specifically are: 1-N-[(S,S,S,R)-2-amino-3,4,5,6-tetrahydroxyhexyl]-sisomicin, 1-N-[(R,S,S,R)-, 1-N-[(S,R,S,R)-, 1-N-[(R,S,R,S)-, 1-N-[(R,R,S,R)- and 1-N-[(S,R,R,R)-2-amino-3,4,5,6-tetrahydrohexyl]-sisomicin, 1-N-[(S,S,S,R)-3-amino-2,4,5,6-tetrahydroxyhexyl]-sisomicin, 1-N-[(S,S,R,S)- and 1-N-[(S,S,S,R)-4-amino-2,3,5,6-tetrahydroxyhexyl]-sisomicin, 1-N-[(S,R,R,R)- and 1-N-[(S,R,R,S)-5-amino-2,3,4,6-tetrahydroxyhexyl]-sisomicin, 1-N-[(S,R,R,R)-, 1-N-[(S,R,S,R)- and 1-N-[(R,R,R)-6-amino-2,3,4,5-tetrahydroxyhexyl)-sisomicin, 1-N-[(S,S,R)-, 1-N-[(R,R,S)-, 1-N-[(R,S,R)-, 1-N-[(S,R,S)- 1-N-[(S,R,R)- and 1-N-[(R,R,R)-2-amino-3,4,5-trihydroxypentyl]-sisomicin, 1-N-[(S,R,S)-, 1-N-[(S,S,R)-, 1-N-[(S,R,R)- and 1-N-[(R,S,S)-3-amino-2,4,5-trihydroxypentyl]-sisomicin, 1-N-[(S,R,S)-4-amino-2,3,5-trihydroxypentyl]-sisomicin, 1-N-[(S,S,S)-, 1-N-[(S,R,R)-, 1-N-[(S,S,R)- and 1-N-[S,S,R)- and 1-N-[(S,R,S)-5-amino-2,3,4-trihydroxypentyl]-sisomicin, 1-N-[(S,S,R,R)- and 1-N-[(S,R,R,R)-2-amino-3,4,5-trihydroxyhexyl]-sisomicin, 1-N-[(S,S,R,R)-4-amino-2,3,5-trihydroxyhexyl]-sisomicin, 1-N-[(S,R,S,R)-3-amino-2,4,5-trihydroxyhexyl]-sisomicin, 1-N-[(S,S,R,S)-5-amino-2,3,4-trihydroxyhexyl]-sisomicin and 1-N-[(S,S,S)-6-amino-2,3,4-trihydroxyhexyl]-sisomicin, 1-N-[(S,S)-3-amino-4,5-dihydroxypentyl]-sisomicin, 1-N-[(S,R,S,R)-2,3-diamino-4,5,6,-trihydroxyhexyl]-sisomicin, 1-N-[(S,R,R,R)-2,6-diamino-3,4,5-trihydroxyhexyl]-sisomicin, 1-N-[(S,S,S,R)-3,6-diamino-2,4,5-trihydroxyhexyl]-sisomicin, 1-N-[(S,R,S,S)-2,4-diamino-3,5,6-trihydroxyhexyl]-sisomicin, 1-N-[(R,R,R)-2,3-diamino-4,5-dihydroxypentyl]-sisomicin, 1-N-[(S,R,S,R)-2-methylamino-3,4,5,6-tetrahydroxyhexyl]-sisomicin, 1-N-[(S,R,S,R)-3-methylamino-2,3,4,6-tetrahydroxyhexyl]-sisomicin, 1-N-[(S,R,R,S)-5-methylamino-2,3,4,6-tetrahydroxyhexyl]-sisomicin, 1-N-[(S,R,S,R)-6-hydroxyethylamino-2,3,4,5-tetrahydroxyhexyl]-sisomicin, 1-N-[(S,S,R)-2-methylamino-3,4,5-trihydroxypentyl]-sisomicin, 1-N-[(S,S,S)-3-methylamino-2,4,5-trihydroxypentyl]-sisomicin, 1-N-[(S,R,S)-4-methylamino-2,3,5-trihdroxypentyl]-sisomicin, 1-N-[(S,R,R)-5-methylamino-2,3,4-trihydroxypentyl]-sisomicin, 1-N-[(S,S,R)-3-dimethylamino-2,5-dihydroxypentyl]-sisomicin, 1-N-[(S,R,S,R)-2-ethoxycarbonylamino-3,4,5,6-tetrahydroxyhexyl]-sisomicin, 1-N-

[(S,R,S,R)-2-acetylamino-3,4,5,6-tetrahydroxyhexyl]-sisomicin, 1-N-[(S,R,S,R)-6-acetylamino-2,3,4,5-tetrahydroxyhexyl]-sisomicin, 1-N-[(S,S,R)-3-acetylamino-2,4,5-trihydroxypentyl]-sisomicin, 1-N-[(S,R,S)-4-acetylamino-2,3,5-trihydroxypentyl]-sisomicin and 1-N-[(S,S,R)-5-acetylamino-2,3,4-trihydroxypentyl]-sisomicin, 1-N-[(S,R,R)-5-amino-2,3,4-trihydroxy-6-methoxyhexyl]-sisomicin, 1-N-[(S,S,R)-3-amino-2,4,5-trihydroxypentyl]-6'-N-hydroxyethyl-sisomicin, 1-N-[(S,R,S)-4-amino-2,3,5-trihydroxypentyl]-6'-N-aminoethyl-sisomicin and 1,6'-di-N-[(S,R,R)-5-amino-2,3,4-trihydroxypentyl]-sisomicin.

According to the present invention there are further provided processes for the production of compounds of the invention in which (a) a compound of the formula

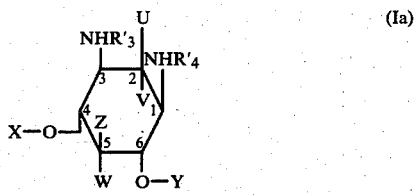

(Ia)

in which

U, V, W, X, Y and Z have the above-mentioned meanings and in which $R_1$, $R_2$, $R_3'$, $R_4'$, $R_5$ and $R_6$ independently denote a hydrogen atom, —SR' or —CO—A', with the proviso that at least one of the radicals $R_1$, $R_2$, $R_3'$, $R_4'$, $R_5$ and $R_6$ denotes a hydrogen atom, and at least one of the radicals $R_1$, $R_2$, $R_3'$, $R_4'$, $R_5$ and $R_6$ denotes —SR' or —CO—A', in which R' denotes an optionally substituted phenyl or di- or tri-phenylmethyl radical and A' denotes $CHal_3$, $-(CH_2)_{n6}-D$ or

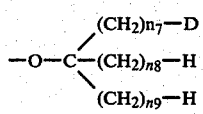

in which

Hal denotes a fluorine, chlorine or bromine atom,

D denotes a hydrogen atom or an optionally substituted phenyl radical, and $n_6$, $n_7$, $n_8$ and $n_9$ independently of one another are 0, 1, 2, 3, 4 or 5, is reacted with an aldehyde of the general formula

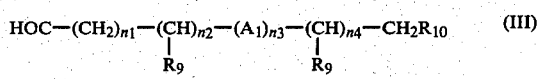

(III)

in which $n_1$, $n_2$, $n_3$ and $n_4$ have the meaning already given, $A_1$ denotes

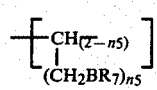

each $R_9$ independently denotes $OR_7$, NH-acyl, $NR_{11}$—SR' or $NR_{11}CO$—A'

$R_{10}$ denotes a hydrogen atom or $R_9$, $R_{11}$ denotes a hydrogen atom or an alkyl group, or two radicals $R_{11}$ together denote alkylidene, and $n_5$, $R_7$ R' and A' have the above-mentioned meaning, with the condition that at least one $R_9$ denotes NH-acyl $NR_{11}$—SR' or $NR_{11}CO$—A' and the number of groups NH-acyl, $NR_{11}$—SR' and $NR_{11}CO$—A' does not exceed 2, in the presence of a hydrogen donor reducing agent and the protective groups —SR' or —CO—A' and, if appropriate, acyl groups are then split off, or (b) a compound of formula (I) as defined above is reacted with a epoxy compound of the general formula

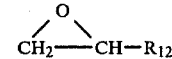

in which $R_{12}$ denotes

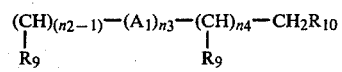

and $A_1$, $R_9$, $R_{10}$, $n_2$, $n_3$ and $n_4$ have the above-mentioned meanings, and the protective groups —SR' or COA' are then split off.

Optionally substituted phenyl R' is, in particular, phenyl or phenyl which is substituted by one, two or three substituents from the series comprising nitro, $C_1$-$C_4$-alkyl, $C_1$-$C_4$-alkoxy, $C_1$-$C_4$-alkoxycarbonyl and phenyl or by 1 to 5 halogen atoms preferably chlorine, bromine or fluorine atoms.

Optionally substituted phenyl D is, in particular, phenyl or phenyl which is substituted by one, two or two substituents from the series comprising nitro, $C_1$-$C_4$-alkyl, $C_1$-$C_4$-alkoxy, phenyl and halogen.

The compounds of the formula (Ia) are obtained, for example, by reacting sisomicin with o-nitrophenyl-sulphenic acid p-nitrophenyl ester in an inert organic or inorganic solvent, if appropriate with the addition of water, at temperatures between $-30°$ and $+50°$ C. in the presence of a base. In this reaction, one to four mols of the sulphenic acid ester are employed per one mol of sisomicin, depending on how many amino groups are to be protected. Further reagents with which protective groups can be introduced are tritylsulphenyl chloride, o-nitrophenylsulphenyl chloride, 2-4-dinitrophenylsulphenyl chloride, 2,4,5-trichlorophenylsulphenyl chloride, pentachlorophenylsulphenyl chloride, 2,4-dinitrophenylsulphenic acid p-nitrophenyl ester, 2,4,5-trichlorophenylsulphenic acid p-nitrophenyl ester, pentachlorophenylsulphenic acid p-nitrophenyl ester, acetic anhydride, trichloroacetic anhydride, acetyl chloride, di-t-butyl pyrocarbonate and diethyl pyrocarbonate.

The sulphenyl protective groups can be split off with weak acids or, preferably, with nucleophiles, preferably with nucleophiles containing H—S groups, such as $H_2S$, thiophenol or 2-mercaptobenzthiazole, in a suitable organic solvent, such as methylene chloride, methanol or mixtures of such solvents. The remaining protective groups can be split off with aqueous alkali metal hydroxide or alkaline earth metal hydroxide or with acids such as trifluoroacetic acid, perchloric acid or boron trifluoride-etherate.

In the case of reaction variant (a), the reductive alkylation with an aldehyde of the formula (III) in the presence of a hydrogen donor reducing agent is carried out at room temperature or at elevated temperature, up to about 80° C., depending on the reactivity of the aldehyde. It can be carried out in the presence of air, although it can be more favourable to carry out the reaction under an inert gas (preferably argon or nitrogen). The end of the reaction can be established by determination by thin layer chromatography.

Hydrogen donor reducing agents which are used in this process include dialkylaminoboranes, for example dimethylaminoborane, diethylaminoborane and morpholinoborane, tetraalkylammonium cyanoborohydrides, for example tetrabutylammonium cyanoborohydride, alkali metal borohydrides, for example sodium borohydride, and, preferably, alkali metal cyanoborohydrides, for example lithium cyanoborohydride and sodium cyanoborohydride.

The process is preferably carried out in an inert solvent. The solvent can be an organic solvent or an inorganic solvent, in which the selectively protected 4,6-di-O-(aminoglycosyl)-1,3-diaminocyclitol and the other reagents are soluble. Although anhydrous aprotic solvents can advantageously be employed, for example tetrahydrofurane if the reducing agent is morpholinoborane, aprotic solvent is nevertheless usually used. A suitable protic solvent is, for example, a $C_1$ to $C_6$ alkanol or, preferably, water or an aqueous $C_1$ to $C_4$ alkanol, preferably aqueous methanol or ethanol, or acetone or other solvent systems which contain water, such as aqueous dimethylformamide, aqueous hexamethylphosphoramide, aqueous tetrahydrofurane or aqueous ethylene glycol dimethyl ether.

The process is preferably carried out in a pH range from 1 to 11, and more preferably at pH 3.5 to 8.

The aldehydes used in the process are amino-sugar derivatives. In most cases, they are accessible by known syntheses, such as are described, for example, in "Methods in Carbohydrate Chemistry". Academic Press—New York and London—Volume I, 206-257 (1962) and Vol. VI, 208-282 (1972). They can be employed for the reductive alkylation either in the free form or as acetals—for example as dimethyl acetals of the formula

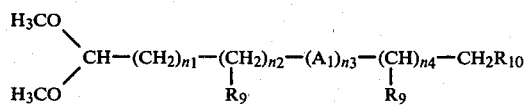

wherein $R_9$, $R_{10}$, $A_1$, $n_1$, $n_2$, $n_3$ and $n_4$ have the meaning already given.

When acetals are used, the reaction is carried out in the presence of mineral acids or organic acids such as acetic acid, whereupon the acetal is split and the aldehyde liberated reacts immediately with the appropriate amino group of the aminotrisaccharide derivatives.

An important advantage of the use, according to the invention, of carbohydrates or derivatives thereof for introducing aminopolyhydroxyalkyl radicals under reduction is the fact that in the form of the amino-sugars or N-protected derivatives thereof, a large number of polyfunctional and above all optically pure aldehyde compounds are available for reductive alkylation reactions. It should be particularly taken into consideration that the biological properties of the pure components of diastereomer mixtures of the aminoglycoside antibiotics according to the invention usually differ from one another significantly.

The following N-blocked amino-sugars used according to the process of the invention and merely mentioned by way of illustration are N-acylated or N-sulphenylated derivatives of, for example, 4-amino-D-erythrose, 4-amino-4-desoxy-L-lyxose, 3-amino-3-desoxy-D-ribose, 2-amino-2-desoxy-D-ribose, 6-amino-6-desoxy-D-glucose, 5-amino-5-desoxy-L-idose, 4-amino-4-desoxy-D-galactose, 3-amino-3-desoxy-D-glucose, 2-amino-2-desoxy-D-mannose, 3-amino-2,3-didesoxy-D-ribose, 2,6-diamino-2,6-didesoxy-D-glucose, 3,6-diamino-3,6-didesoxy-D-allose-2-methylamino-2-desoxy-D-glucose, 3-methylamino-3-desoxy-D-glucose, 3-methylamino-3-desoxy-D-ribose or 5-methylamino-5-desoxy-D-ribose.

The N-acylated or N-sulphenylated compounds are prepared as described earlier.

If N-blocked amino-sugars which carry alkyl, acyl or alkylidene radicals on one or more OH groups, as well as on the 1-OH group, are used, compounds of the formula (I) with alkoxy, acyloxy or O-alkylidene radicals in the newly introduced group R are obtained after splitting off the amino-protective groups. Examples of such amino-sugar derivatives are N-blocked 2-amino-2-desoxy-6-O-methyl-D-glucose and 5-amino-5-desoxy-2,3,-O-isopropylidene-D-ribose. The radicals indicated in the case of formula (II) are used here as the amino-protective groups.

It is particularly preferred according to reaction variant (a) that selectively blocked amino-sugar derivatives of the type

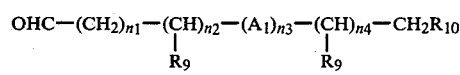

wherein $R_9$, $R_{10}$, $A_1$, $n_1$, $n_2$, $n_3$ and $n_4$ have the meaning already given,
which are in the aldehyde form and not in the hemiacetal form, are employed as the aldehyde component for reductive alkylation of the selectively protected aminotrisaccharides, all the O- and N-protective groups present in the molecule being then split off and compounds of the formula (I) thus obtained.

In the case of reaction variant (b), where the epoxy compounds are relatively slow to react, the reaction is appropriately carried out at elevated temperature. The reaction concerned otherwise proceed by known methods.

After splitting off the protective groups present in the molecule, compounds of the formula (I) which are substituted by —$CH_2$—CHOH—$R_{12}$ on one or two of the N atoms present, and in which $R_{12}$ has the meaning indicated, are thus obtained.

The present invention also includes a process for the preparation of N-(amino-polyhydroxyalkyl)-aminotrisaccharides of the formula (I), in which the 4,6-di-O-(aminoglycosyl)-1,3-diaminocyclitols are reacted, in the unprotected form—that is to say as the free base or as acid addition salts thereof—with the aldehydes of the formula (III) used according to the invention and a hydrogen donor reducing agent. In this process, the appropriate aminotrisaccharides of the formula (I) in which, in this case, $R_1$ to $R_6$ represent hydrogen, or acid addition salts thereof, in which some of the amino groups present in the molecule are neutralised by mineral acids, are reacted with one to two equivalents of N-blocked amino-polyhydroxyaldehyde of formula (II) in the presence of a hydrogen donor reducing agent, such as sodium cyanoborhydride or dimethylaminoborane, in a suitable solvent. After the reaction, the amino-protective groups present in the aldehyde used, of the formula (III), are split off in the manner described above and the N-(amino-polyhydroxyalkyl)-aminotrisaccharides of the formula (I) are isolated, for which, in some cases, it may be necessary to separate off the desired end products from undesired by-products by column chromatography.

The compounds according to the invention are antimicrobial agents with a broad spectrum of action and a particular activity against Gram-negative bacteria, for example *E. coli,* Proteus, Klebsiella and Pseudomonas. Inhibition areolae in the agar hole test were found, for example, against the following bacteria strains, at a concentration of 100 micrograms/1 ml: *Pseudomonas aerug.* 5737, *Pseudomonas aerug.* F 41, *Klebsiella pneum.* Munich, *Klebsiella pneum.* 1 Düsseldorf, *E. coli Munster*[2] and *E. coli Neumann.*

The invention also relates to the use in medicine of the compounds of the invention in cases of bacterial infection.

The present invention provides a pharmaceutical composition containing as active ingredient a compound of the invention in admixture with a solid, liquid or liquefied gaseous diluent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate, (e) agents for retarding dissolution, e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocao oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders are sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile and, if appropriate, blood-isotonic.

The pharmaceutical compositions which are suspensions can contain the usual diluent, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include inert solvents.

The discrete coherent portions constituting the medicament according to the invention will generally be adapted by virtue of their shape or packaging for medical administration and may ne, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally (e.g. as solutions or suspensions for use in ears and eyes), preferably locally or parenterally (especially intramuscularly). Preferred pharmaceutical compositions and medicaments are therefore those adapted for administration such as local or parenteral administration. Administration in the method of the invention is preferably local or parenteral administration.

The dosage of the compounds according to the invention is usually similar to the dosage of the 1-N-unsubstituted compounds. In general it has proved advantageous to administer amounts of from 20 mg/day/animal to 2,000 mg/day/animal, preferably 100 mg to 500 mg/day, to achieve effective results.

In general, topical preparations contain 0.1 to 3.0 g of the compounds of the invention per 100 g of ointment, cream or lotion. Topical administration normally takes place 2 to 5 times daily.

Injection solutions or suspension are usually administered such that the infected organism receives 1 to 15 mg of active compound per kilogram of body weight in 2 to 4 doses per day. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following formulations illustrate pharmaceutical compositions according to the present invention.

| Formulation 1 Tablet | 10 mg tablet | 25 mg tablet | 100 mg tablet |
|---|---|---|---|
| Compound of Example 8 | 10.50+ mg | 26.25+ mg | 105.00+ mg |
| Lactose | 197.50 mg | 171.25 mg | 126.00 mg |
| Maize starch | 25.00 mg | 25.00 mg | 35.00 mg |
| Polyvinylpyrrolidone | 7.50 mg | 7.50 mg | 7.50 mg |
| Magnesium stearate | 2.50 mg | 2.50 mg | 3.50 mg |

+5% excess

To produce the tablets, a suspension of the active compound in question, lactose and polyvinylpyrrolidone is prepared and this suspension is spray-dried. The maize starch and magnesium stearate are added and the mixture is pressed to tablets.

| Formulation 2 Ointment | |
|---|---|
| Compound of Example 8 | 1.0 g |
| Methylparaben U.S.P. | 0.5 g |
| Propylparaben U.S.P. | 0.1 g |
| Petrolatum | to 1,000 g |

Preparation (1) The petrolatum is melted
(2) the active compound, Methylparaben and Propylparaben are mixed with about 10% of the molten petrolatum,
(3) the mixture is introduced into a colloid mill and
(4) the remaining petrolatum is added, whilst stirring, and the mixture is cooled until it becomes semi-solid. The product is filled into suitable containers.

| Formulation 3 Injection solution | per 2.0 ml phial | per 50 liters |
|---|---|---|
| Compound of Example 8 | 84.0 mg+ | 2,100.0 gm |
| Methylparaben, U.S.P. | 3.6 mg | 90.0 gm |
| Propylparaben, U.S.P. | 0.4 mg | 10.0 gm |
| Sodium bisulphite, U.S.P. | 6.4 mg | 160.0 gm |
| Disodium ethylenediaminetetraacetate-dihydrate | 0.2 mg | 5.0 mg |
| Water, U.S.P. q.s. | 2.0 mg | 50.0 liters |

+5% excess

The following Examples illustrate the preparation of compounds according to the present invention.

EXAMPLE 1

1,2',3,6'-Tetra-N-acetyl-sisomicin 1.1 g of sisomicin are dissolved in 120 ml of water. After adding 60 ml of methanol, 2.5 ml of acetic anhydride are added dropwise, whilst stirring. After 15 minutes, the mixture is evaporated to dryness in vacuo. The residue is dissolved in 10 ml of methanol and this solution is added dropwise to a mixture of 30 ml of ether and 30 ml of petroleum ether, whereupon the desired product precipitates. Yield=1.43 g, MS: m/e=615.

$^{13}$C—NMR (CD$_3$OD); $\delta$=50.14 (C-1); 49.20 (C-3); 46.88 (C2'); 42.26 (C-6') and 173.24, 173.13 and 172.63 ($>$C=O) ppm.

EXAMPLE 2

1,3,3″,6′-Tetra-N-ethoxycarbonyl-sisomicin 450 mg of sisomicin are dissolved in 10 ml of water. After adding 10 ml of methanol, 870 mg of pyrocarbonic acid di-ethyl ester are added, whilst stirring thoroughly. After stirring the mixture at room temperature for 1.3 hours, 5 ml of water are added, the mixture is filtered and the filtrate is evaporated to dryness in vacuo. The residue is dissolved in methanol and the desired product is precipitated by adding ether and petroleum ether. Yield=600 mg.

$^{13}$C—NMR (CD$_3$OD) δ=66.01 (C-3″); 52.23 (C-1); 51.67 (C-3); 48.23 (C-2′); 43.74 (C-6′); and 157.69 (C=O) ppm.

EXAMPLE 3

2′,3,3″6′-Tetra-N-(o-nitrophenylsulphenyl)-sisomicin

(3a) Penta-N-(o-nitrophenylsulphenyl)-sisomicin 38 g (0.10 mol) of o-nitrophenylsulphenyl chloride in 200 ml of dioxane, and 260 ml of 1 N NaOH are added to 13.84 g (20 mmols) of sisomicin sulphate in 100 ml of 1 N NaOH and 450 ml of freshly distilled dioxane such that the pH is between 12 and 14. The precipitate is filtered off and dissolved in CH$_2$Cl$_2$/H$_2$O and the CH$_2$Cl$_2$ phase is dried with Na$_2$SO$_4$.

CH$_2$Cl$_2$ is added to the filtrate, the aqueous phase is discarded and the organic phase is dried over Na$_2$SO$_4$. The combined organic phases are evaporated to dryness and filtered over 250 g of silica gel (column diameter: 8 cm), first with CH$_2$Cl$_2$ and then with CH$_2$Cl$_2$/MeOH=97.5/2.5. The eluate gives, after evaporating off the solvent, 22 g (91% of penta-N-(o-nitrophenylsulphenyl)-sisomicin as an orange-coloured foam. 13-C—NMR (CDCl$_3$): δ=124–148 (aromatic H); 102.30 (C-1″); 99.00 (C-1′); 97.91 (C-4′); 89.05 (C-6′); 82.33 (C-4); 57.31 (C-1) and 56.73 (C-3) ppm.

(3b) 3″-N-(o-Nitrophenylsulphenyl)-sisomicin 160 ml of thiophenol are added to 16.0 g (13.2 mmols) of penta-N-NPS-sisomicin (NPS represents o-nitrophenylsulphenyl) in 80 ml of absolute pyridine and, after 1 hour, the mixture is poured onto 500 ml of diethyl ether, the precipitate is taken up in methylene chloride/methanol=8/2 and the mixture is filtered over silica gel (column: 5.5×12 cm, running agent, methylene chloride/methanol=8/2, increasing addition to the running agent mixture methanol/methylene chloride/20% strength ammonia=4/2/1); the red zone gives after evaporating off the solvent, 6.6 g (83%) of 3″-N-o-nitrophenylsulphenyl-sisomicin as a deep red foam.

13-C—NMR (CD$_3$OD); 33.59 (CH$_3$N); 52.23 (C-1); 51.16 (C-3 53 (C-2′) and 43.84 (C-6′) ppm.

(3c) 2′,3,3″,6′-Tetra-N-(o-nitrophenylsulphenyl)-sisomicin and 1,2′,3″,6′-tetra-N-(o-nitrophenylsulphenyl)-sisomicin 4.4 g (15.0 mmols) of o-nitrophenylsulphenic acid p-nitrophenyl ester in 85 ml of methylene chloride are added to 3.0 g (5.0 mmols) of 3″-N-NPS-sisomicin in 5 ml of methanol and 45 ml of methylene chloride, the reaction is immediately evaporated to dryness, the residue is taken up in methylene chloride and the methylene chloride mixture is chromatographed on silica gel (column: 5.5×30 cm) with 200 ml of methylene chloride and then with methylene chloride/methanol. 500 fractions are collected, combined fractions 150 to 250 giving 1,2′,3″,6′-tetra-NPS-sisomicin and fractions 270 to 500 giving the 2′,3,3″,6′-tetra-NPS derivative, in each case as an orange-coloured foam.

1,2′,3″,6′-Tetra-NPS-sisomicin:
R$_F$(CH$_2$Cl$_2$/CH$_3$OH=9/1): 0.62.
IR (KBr): 1501, 1360 and 1300 (strong); 1587, 1562 and 755 (medium); and 1442, 780 and 890 (weak).

2′,3,3″,6′-Tetra-NPS-sisomicin:
R$_F$(CH$_2$CH/CH$_3$OH=9/1): 0.42.
IR (KBr): 1500, 1358 and 1206 (strong); 1586, 1560 and 753 (medium); and 1442, 890 and 779 (weak).

EXAMPLE 4

3″-N-(o-Nitrophenylsulphenyl)-2′3,6′-tris-N-trichloroacetyl-sisomicin

EXAMPLE 4a

Penta-N-(o-nitrophenylsulphenyl)-2″-O-[dimethyl-(1,2-dimethyl-propyl-silyl]-sisomicin 60.6 g of crude penta-N-(o-nitrophenylsulphenyl)-sisomicin and 8.75 g of imidazole are dissolved in 250 ml of absolute methylene chloride. 22.5 ml of dimethyl-(1,2-dimethyl-propyl)-silyl chloride are added dropwise at 0° C., with the exclusion of moisture. The batch is evaporated down to about 170 ml in vacuo and is left to stand at room temperature for 48 hours. After adding 130 ml of absolute methylene chloride, the precipitate is filtered off, the filtrate is throughly shaken vigorously with 350 ml of petroleum ether and the petroleum ether phase is decanted off and discarded. The oil which has precipitated is dissolved in 100 ml of methylene chloride, reprecipitated with 250 ml of petroleum ether and finally dried under a high vacuum. Yield: 60 g (89%) of crude product, which can be employed for the subsequent reactions without further purification. A pure product is obtained by chromatography on silica gel with CH$_2$Cl$_2$/CH$_3$OH=99/1.

R$_F$(CH$_2$Cl$_2$/CH$_3$OH=99.5/0.5): 0.62.
13-C—NMR (CDCl$_3$): δ=124–138 (aromatic C); 147.54 (C-5′); 102.26 (C-1″); 97.81 (C-4′); 99.09 (C-1′); −2.9 to −3.0 (Si—CH$_3$); 22.77

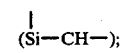

and 30.60

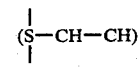

ppm.

Penta-N-(o-nitrophenylsulphenyl)-2″,5-bis-O-[dimethyl-(1,2-dimethyl-propyl)-silyl]-sisomicin is isolated as a by-product.

R$_F$(CH$_2$Cl$_2$/CH$_3$OH=99.5/0.5): 0.79.
13-C—NMR (CDCl$_3$): δ=124–146 (aromatic C); 148.00 (C-5′); and 96.13 (C-4′) ppm.

EXAMPLE 4b

1,3″-Bis-N-(o-nitrophenylsulphenyl)-2″-O-[dimethyl](1,2-dimethyl-propyl)-silyl]-sisomicin 16 g of 2-mercaptobenzthiazole are added to 56 g of crude penta-N-(o-nitrophenylsulphenyl)-2″-O-[dimethyl-(1,2-dimethyl-propyl)-silyl]-sisomicin in 36 ml of methylene chloride/70 ml of methanol, the mixture is shaken until a clear solution is obtained and the solution is left to stand at 5° C. for 2 hours. The precipitate which thereby separates out is filtered off and the solution is used for further reactions without isolating the desired product. The yield is about 80% of theory. To prepare a pure product, the filtrate is evaporated rapidly in vacuo and the residue is chromatographed on silica gel with (a) methylene chloride, (b) methylene chloride/CH$_3$OH (8:2) and (c) with CH$_2$Cl$_2$/CH$_3$OH/20% strength aqueous ammonia (7:2.7:0.3). The yield of pure product is 25.3 g (69%).

R$_F$ (CH$_2$Cl$_2$/CH$_3$OH/20% strength aqueous NH$_3$=7:2.7:0.3)=0.66.

13-C—NMR (CD$_3$OD): δ=1.5 (Si—CH$_3$); 122–146 (aromatic C); 147.14 (C-5'); 103.31 (C-1''); 100.16 (C-1') and 99.30 (C-4') ppm.

EXAMPLE 4c 1,3''-Bis-N-(o-nitrophenylsulphenyl)-2'3,6'-tris-N-trichloroacetyl-2''-O-[dimethyl-(1,2-dimethyl-propyl)-silyl]-sisomicin 7.5 ml of trichloroacetic anhydride are added dropwise to 8.8 g of 1,3''-bis-N-(o-nitrophenylsulphenyl)-2''-O-[dimethyl-(1,2-dimethyl-propyl)-silyl]-sisomicin in 20 ml of methylene chloride/20 ml of pyridine at −15° C. and stirring is continued for a further 10 minutes at room temperature. After adding 20 ml of methylene chloride, the batch is extracted twice by shaking with 20 ml of H$_2$O each time, the organic phase is evaporated and the residue is further processed as the crude product.

R$_F$ (CH$_2$Cl$_2$/CH$_3$OH=97.5/2.5)=0.72.

EXAMPLE 4d 1,3''-Bis-N-(o-nitrophenylsulphenyl)-2',3,6'-tris-N-trichloroacetyl-sisomicin The crude oil from Example 4c is dissolved in 20 ml of dimethylsulphoxide, 2 ml of a 50% strength KF solution are added and the mixture is stirred vigorously for 3 hours. The product is precipitated with water, washed with water and dried. The crude product is further processed without additional purification.

R$_F$ (CH$_2$Cl$_2$/CH$_3$OH=97.5/2.5)=0.42.

13-C—NMR (CDCl$_3$): δ=103.60 (C-1''); 66.48 (C-3''); 55.15 (C-1); 50.60 (C-3); 79.86 (C-4); 76.18 (C-5); 89.16 (C-6); 97.74 (C-1'); 96.84 (C-4'); 149.80 (C-5); 92.78 (CCl$_3$); and 162.29 and 162.11 (CO) ppm.

EXAMPLE 4e

3''-N-(o-Nitrophenylsulphenyl)-2',3,6'-tris-N-trichloroacetyl-sisomicin

The product from Example 4d is dissolved in 13 ml of methylene chloride, the solution is shaken with 26 ml of methanol and 5 g of 2-mercaptobenzthiazole until a clear solution is obtained and this solution is left to stand at 5° C. for 3 days. The precipitate is filtered off, the filtrate is evaporated and the residue is chromatographed on silica gel.

Running agent a: CH$_2$Cl$_2$/CH$_3$OH=95/5; b) (CH$_2$Cl$_2$/CH$_3$OH/20% strength aqueous NH$_3$=93/6.5/0.5).

R$_F$ (CH$_2$Cl$_2$/CH$_3$OH/20% strength aqueous NH$_3$=93/6.5/0.5): 0.43.

13-C—NMR (CDCl$_3$): δ=103.43 (C-1''); 67.46 (C-3''); 50.85 (C-1); 50.28 (C-3); 79.44 (C-4); 76.51 (C-5); 89.29 (C-6); 97.61 (C-1'); 96.62 (C-4'); 149.50 (C-5'); 92.46 and 92.38 (C-4'); and 162.01 and 161.76 (CO) ppm.

EXAMPLE 5

3''-N-(o-Nitrophenylsulphenyl)-2'3,6'-tris-N-acetyl-sisomicin

EXAMPLE 5a 1,3''-Bis-N-(o-Nitrophenylsulphenyl)-2',3,6'-triacetyl-2''-O-[dimethyl-(1,2-dimethyl-propyl)-silyl]-sisomicin 15 ml of acetic anhydride and 38 ml of 6 N NaOH are added to the crude solution of 1,3''-bis-N-(o-nitrophenylsulphenyl)-2''-O-[dimethyl-(1,2-dimethyl-propyl)-silyl]-sisomicin in the course of 2 minutes, whilst cooling with ice, such that the reaction mixture always remains alkaline. The batch is evaporated in vacuo until the crude oil settles as a clear layer. The aqueous phase is decanted off and the oil is stirred with 120 ml of H$_2$O in vacuo at 30°–40° C. such that some (about 20–30 ml) of the water is distilled off. The aqueous phase is decanted off and the oil is further processed without purification. Chromatography on silica gel with CH$_2$Cl$_2$/CH$_3$OH=95/5 gives a pure product.

R$_F$ (CH$_2$/Cl$_2$/CH$_3$OH=95/5): 0.18; and (CH$_2$Cl$_2$/CH$_3$OH=90/10): 0.7.

H—NMR (220 MHz): δ=2.02, 1.92 and 1.89 (CH$_3$—CO); and 3.03 (N-CH$_3$) ppm.

EXAMPLE 5b 1,3''-Bis-N-(o-nitrophenylsulphenyl)-2',3,6'-triacetyl-sisomicin (a) Starting from 1,3''-bis-N-(o-nitrophenylsulphenyl)-2'2,6'-triacetyl-2''-O-[dimethyl-(1,2-dimethylpropyl)-silyl]-sisomicin.

The unpurified oil obtained according to Example 5a is dissolved in 100 ml of dimethylsulphoxide (DMSO), 8.75 ml of a 50% strength aqueous KF solution are added and the mixture is stirred vigorously. After 2 hours, the batch is poured onto 300 g of ice, the precipitate is allowed to settle and the aqueous DMSO phase is carefully decanted. The residue is stirred with 100 ml of water, the aqueous phase is decanted and the residue is dried under a high vacuum. 28 g (76%, relative to penta-N-(o-nitrophenylsulphenyl)-2''-O-[dimethyl-(1,2-dimethylpropyl)-silyl]-sisomicin according to Example 4a) of crude product, which can be further purified by chromatography on silica gel with CH$_2$Cl$_2$/CH$_3$OH=95/5, are obtained.

3''-N-(o-Nitrophenylsulphenyl)-2',3,6'-tris-N-acetyl-sisomicin 28 g of the crude product from Example 5b are dissolved in 56 ml of methylene chloride, 18 g of 2-mercaptobenzthiazole and 93 ml of methanol are added and the mixture is shaken vigorously until a clear solution has formed. The batch is kept at 5° C. for 20 hours, and 16 ml of 12% strength H$_2$O$_2$ solution are added dropwise. The precipitate is filtered off and the filtrate is evaporated in vacuo. A red foam which can be employed for most of the subsequent reactions without further purification is obtained. The yield is 26.8 g (88.6%, relative to crude penta-N-(o-nitrophenylsulphenyl)-2''-O-[dimethyl-(1,2-dimethyl-propyl)-silyl]-sisomicin according to Example 4a). The foam consists of the desired product to the extent of 57%, that is to say the total yield, relative to Example 4a, is 51% of theory. For further purification, 3 g of the crude product are chromatographed on silica gel [column 3.8×30 cm, running agent: CH$_2$Cl$_2$/CH$_3$OH=9/1 with increasing addition (5% at the end) of a mixture of CH$_2$Cl$_2$/CH$_3$OH/20% strength aqueous NH$_3$=2/4/1]. The yield is 1.4 g.

R$_F$ (CH$_2$/CH$_3$OH/20% strength aqueous NH$_3$=7.5:2.4:0.15):0.79.

13-C—NMR (d6-DMSO): δ=71.70 (C-2''); 50.89 (C-1); 47.73 (C-3); 80.95 (C-4); 74.79 (C-5); 86.53 (C-6); 45.52 (C-2'); 96.55 (C-1'); 146.78 (C-5'); and 169.23, 168.94 and 169.64 (3×CO) ppm.

In the following embodiment Examples, the following running agent systems were utilised to determine the Rf value:

Running agent system G=methylene chloride:methanol:15% strength aqueous ammonia (1:1:1), the lower phase of this with the addition of 1% of methanol.

Running agent system E=methylene chloride:methanol:20% strength aqueous ammonia (2:4:1).

Running agent system P=chloroform:methanol:acetone:20% strength aqueous ammonia (2:2:1:1).

Running agent system B=methylene chloride:methanol:20% strength aqueous ammonia (5:5:1).

The thin layer chromatography was carried out on pre-coated silica gel plates from Messrs. E. Merck, Darmstadt. Silica gel 60 from Messrs. E Merck was used for the column separations.

EXAMPLE 6

1-N-[(S,R,S,R)-2-ethoxycarbonylamino-2-desoxy-3,4,5,6-tetrahydroxyhexyl]-3''-N-(o-nitrophenylsulphenyl)-2',3,6'-tri-N-trichloroacetyl-sisomicin 600 mg of 3''-N-(o-nitrophenylsulphenyl)-2',3,6'-tri-N-trichloroacetyl-sisomicin and 200 mg of 2-ethoxycarbonylamino-2-desoxy-D-glucose are dissolved in 6 ml of methanol and 1 ml of water and, after the mixture has been adjusted to pH 5.5 by adding 50% strength acetic acid, it is stirred at room temperature for 30 minutes. 200 mg of sodium cyanoborohydride are then added and the mixture is heated to 60° C. for five hours.

For working up, the solvent is evaporated off in vacuo. The residue is taken up in 2 ml of methanol and 10 ml of methylene chloride and the mixture is washed with 10 ml of water. The organic phae is dried with sodium sulphate. It contains the desired compound as the main product.

Rf value=0.57 (running agent system G).

EXAMPLE 7

1-N-[(S,R,S,R)-2-Ethoxycarbonylamino-2-desoxy-3,4,5,6-tetrahydroxyhexyl]-3''-N-(o-nitrophenylsulphenyl)-sisomicin To split off the trichloroacetyl groups, the solid from Example 6 is dissolved in 9 ml of methanol and 3 ml of water and, after adding 540 mg of barium hydroxide octahydrate, the mixture is heated to 50° C. for 7 hours. The barium salts are removed by precipitation with CO$_2$ and filtration, the filtrate is evaporated in vacuo and the desired compound is isolated from the residue by column chromatography on silica gel with solvent mixture E as the eluting agent. By combining the appropriate fractions, the pure desired compound is obtained as a yellow solid.

Rf value=0.29 (running agent system E).

EXAMPLE 8

1-N-[(S,R,S,R)-2-Ethoxycarbonylamino-2-desoxy-3,4,5,6-tetrahydroxyhexyl]-sisomicin The product from Example 7 is dissolved in 5 ml of methyl chloride and 2.5 ml of methanol, to which 1 ml of a solution of 850 mg of 2-mercaptobenzthiazole in 3 ml of methanol and 5 ml of methylene chloride is added, and the mixture is acidified to pH 1 with hydrochloric acid. 3 ml of water are then added and the mixture is thoroughly shaken vigorously. The aqueous phase, which contains the desired product, is separated off and washed twice more with 2 ml of methylene chloride each time. It is then rendered alkaline by stirring with a basic ion exchanger resin (Lewatit MP 500 ®, BAYER, OH⊖ Form), and is stirred thoroughly with active charcoal and filtered and the filtrate is evaporated in vacuo to give an amorphous solid.

Rf value=0.34 (running agent system P).

EXAMPLE 9

1-N-[(R,R,S,R)-2-Acetylamino-2-desoxy-3,4,5,6-tetrahydroxyhexyl]-3''-N-(o-nitrophenylsulphenyl)-2',3,6'-tri-N-trichloroacetyl-sisomicin 600 mg of 3''-N-(o-nitrophenylsulphenyl)-2',3,6'-tris-N-trichloroacetyl-sisomicin and 200 mg of 2-acetylamino-2-desoxy-D-mannose are dissolved in 6 ml of methanol and 1 ml of water and, after the mixture has been adjusted to pH 5.5 by adding 50% strength acetic acid, it is stirred at room temperature for 30 minutes. 200 mg of sodium cyanoborohydride are then added and the mixture is heated to 60° C. for five hours.

For working up, the solvent is evaporated off in vacuo. The residue is taken up in 2 ml of methanol and 10 ml of methylene chloride and the mixture is washed with 10 ml of water. The organic phase is dried with sodium sulphate. It contains the desired compound as the main product.

Rf value=0.48 (running agent system G).

EXAMPLE 10

1-N-[(R,R,S,R)-2-Acetylamino-2-desoxy-3,4,5,6-tetrahydroxy-hexyl]-3''-N-(o-nitrophenylsulphenyl)-sisomicin To split off the trichloroacetyl groups, the solid from Example 9 is dissolved in 9 ml of methanol and 3 ml of water and, after adding 540 mg of barium hydroxide octahydrate, the mixture is heated to 50° C. for 7 hours. The barium salts are removed by precipitation with CO$_2$ and filtration, the filtrate is evaporated in vacuo and the desired compound is isolated from the residue by column chromatography on silica gel with the solvent mixture E as the eluting agent. By combining the appropriate fractions, the pure desired compound is obtained as a yellow solid.

Rf value=0.32 (running agent system E).

EXAMPLE 11

1-N-[(R,R,S,R)-2-Acetylamino-2-desoxy-3,4,5,6-tetrahydroxyhexyl]-sisomicin

The product from Example 10 is dissolved in 5 ml of methylene chloride and 2.5 ml of methanol, to which 1 ml of a solution of 850 mg of 2-mercaptobenzthiazole in 3 ml of methanol and 5 ml of methylene chloride is added, and the mixture is acidified to pH 1 with hydrochloric acid. 3 ml of water are then added and the mixture is thoroughly shaken vigorously. The aqueous phase, which contains the desired product, is separated off and washed twice more with 2 ml of methylene chloride each time. It is then adjusted to pH 11.5 by stirring with a basic ion exchanger resin (Lewatit MP 500 ®, BAYER, OH⊖ form), and is stirred thoroughly with active charcoal and filtered, and the filtrate is evaporated in vacuo to give an amorphous solid.

$R_f$ value = 0.32 (running agent system P).

EXAMPLE 12

1-N-[(S,R,R,R)-5-Amino-5-desoxy-2,3,4,6-tetrahydroxyhexyl]-sisomicin 200 mg of 3''-N-(o-nitrophenylsulphenyl)-2',3,6'-N-acetyl-sisomicin and 200 mg of 5-acetylamino-5-desoxy-D-glucose in 7 ml of methanol and 1.4 ml of water are heated to 70° C. for 30 minutes. 70 mg of sodium cyanoborohydride are then added and the mixture is heated for a further 60 minutes. It is then allowed to cool to room temperature, 5 ml of water are added an deionisation is effected with a basic ion exchanger resin (Lewatit MP 500 ®, OH⊖ form, BAYER AG, Leverkusen). After filtering, the filtrate is freed from solvent in vacuo.

To split off the protective groups, the residue obtained above is dissolved in 6 ml of water and, after adding 3.6 g of barium hydroxide octahydrate, the mixture is heated under reflux for 5 hours. The barium ions are then precipitated as barium sulphate. The mixture is filtered, the filtrate is deionised with a basic ion exchanger resin (OH⊖ form, see above) and filtered again and the filtrate is evaporated to dryness in vacuo.

The desired compound is thus obtained as an amorphous solid.

$R_f$ value = 0.33 (running agent system B).

EXAMPLE 13

1-N-[(S,R,R,R)-5-Methylamineo-5-desoxy-2,3,4,6-tetrahydroxyhexyl]-sisomicin 300 mg of 3''-N-(o-nitrophenyl)-2',3',6'-tri-N-acetyl-sisomicin and 300 mg of 5-methylamino-5-desoxy-N-acetyl-D-glucose in 10 ml of methanol +2.5 ml of water are heated to 60° C. for 30 minutes. 100 mg of sodium cyanoborohydride are then added and the mixture is heated for a further 90 minutes. It is allowed to come to room temperature, 8 ml of water are added and deionisation is effected with a basic ion exchanger resin. The mixture is filtered and the solvent is evaporated off from the filtrate in vacuo. The residue is dissolved in 5 ml of methanol and 5 ml of methylene chloride, 1 ml of a solution of 850 g of 2-mercaptobenz-thiazole in 3 ml of methanol and 5 ml of methylene chloride is added and the mixture is acidified to pH 1 with hydrochloric acid. 10 ml of water are then added and the mixture is thoroughly shaken vigorously. The aqueous phase—in which the desired N-desulphenylated product is present—is rendered alkaline with a basic ion exchanger resin. The resin is filtered off and the filtrate thus obtained is heated, after adding 4 g of barium hydroxide octahydrate, under reflux for 5 hours to split off the N-acetyl groups. The barium ions are precipitated as barium sulphate, which is filtered off. The filtrate is deionised with a basic ion exchanger. After filtering, the solvent is evapourated off from the filtrate in vacuo and the title compound is obtained as an amorphous solid.

$R_f$ value = 0.35 (running agent system B).

The present invention also comprises pharmaceutically acceptable bioprecursors of the active compounds of the present invention.

For the purposes of this specification the term "pharmaceutically acceptable bioprecursor" of an active compound of the invention means a compound having a structural formula different from the active compound but which nonetheless, upon administration to the animal is converted in the animal's body to the active compound.

What is claimed is:

1. A compound which is a pseudotrisaccharide of the formula

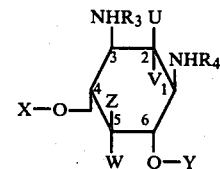

or a pharmaceutically acceptable acid addition salt thereof, in which

X denotes a radical of the formulae

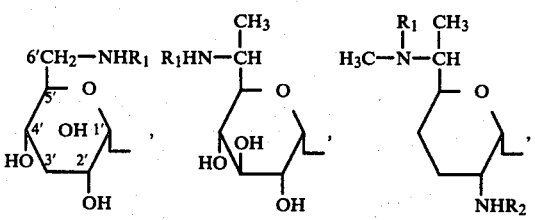

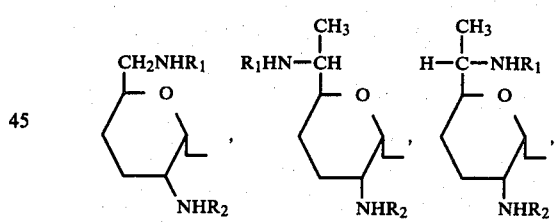

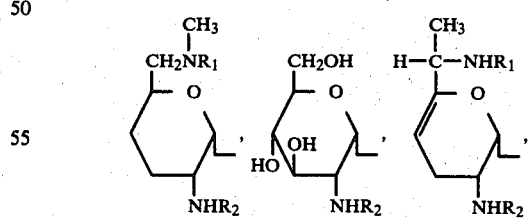

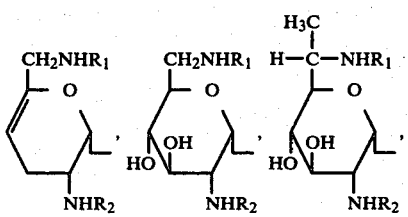

-continued

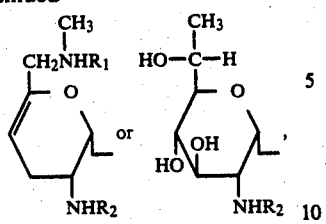

Y denotes a radical of the formula

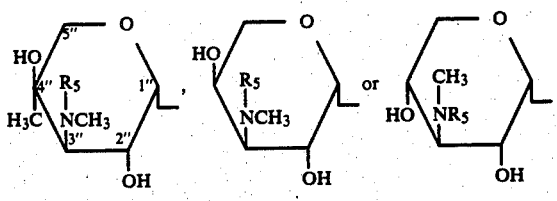

U and V both denote hydrogen atoms, or one denotes a hydrogen atom and one denotes a hydroxyl group and W and Z both denote hydrogen atoms, or one denotes a hydrogen atom and one denotes a hydroxyl group, or Z denotes $NHR_6$ and W denotes a hydrogen atom, and $R_1$, $R_2$, $R_3$, $R_4$, $R_5$ and $R_6$ independently of one another denote a hydrogen atom or an amino-polyhydroxyalkyl radical derived from an amino sugar which is optionally N-protected and optionally carries $C_1$–$C_4$-alkyl, carboxylic acid acyl or $C_1$–$C_6$-alkylidene radicals on one or more OH-groups, at least one of the radicals $R_1$ to $R_5$ being other than hydrogen.

2. A compound according to claim 1 which is derived from one of the antibiotics gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, JI-20A, JI-20B, verdamicin G52, G418, 66-40D, mutamicin 1, mutamicin 2, mutamicin 4, mutamicin 5 and mutamicin 6.

3. A compound according to claim 1, which is a sisomicin derivative of the formula

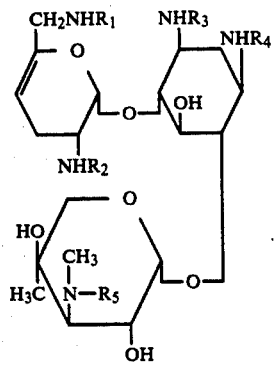

or a pharmaceutically acceptable acid-addition salt thereof in which $R_1$, $R_2$, $R_3$, $R_4$ and $R_5$ have the same meanings as in claim 1.

4. A compound according to claim 1 in which $R_4$ and one of the radicals $R_1$ and $R_2$ are other than a hydrogen atom and the radicals $R_3$, $R_5$, $R_6$ and the other one of the radicals $R_1$ and $R_2$ denote a hydrogen atom.

5. A compound according to claim 1, in which $R_1$, $R_2$, $R_3$, $R_5$ and $R_6$ denote a hydrogen atom and $R_4$ is other than hydrogen.

6. A pharmaceutical composition containing as an active ingredient an antibacterially effective amount of a compound according to claim 1 in admixture with a solid, liquid or liquefied gaseous diluent.

7. A pharmaceutical composition of claim 6 in the form of a sterile or physiologically isotonic aqueous solution.

8. A composition according to claim 6 in the form of an ointment, cream or lotion containing from 0.1 to 3.0 g by weight of the said active ingredient per 100 gm of ointment, cream or lotion.

9. A medicament of claim 6 in the form of tablets, pills, dragees, capsules, ampoules, or suppositories.

10. A method of combating bacterial diseases in warm-blooded animals which comprises administering to the animals an antibacterially effective amount of an active compound according to claim 1 either alone or in admixture with a diluent or in the form of a medicament.

11. A method according to claim 10 in which the active compound is administered in an amount of 100 to 500 mg per day.

12. A method according to claim 10 in which the active compound is administered parenterally in an amount of 1 to 15 mg of active compound per kilogram of body weight.

* * * * *